United States Patent
Dugar

(10) Patent No.: US 11,142,501 B2
(45) Date of Patent: Oct. 12, 2021

(54) PRODRUGS OF MONOMETHYL FUMARATE

(71) Applicant: IXCHEL PHARMA, LLC, Davis, CA (US)

(72) Inventor: Sundeep Dugar, San Jose, CA (US)

(73) Assignee: Ixchel Pharma, Inc., Davis, CA (US)

( * ) Notice: Subject to any disclaimer, the term of this patent is extended or adjusted under 35 U.S.C. 154(b) by 0 days.

(21) Appl. No.: 17/174,450

(22) Filed: Feb. 12, 2021

(65) Prior Publication Data

US 2021/0163414 A1 Jun. 3, 2021

Related U.S. Application Data

(63) Continuation of application No. PCT/US2020/028302, filed on Apr. 15, 2020.

(60) Provisional application No. 62/835,115, filed on Apr. 17, 2019.

(51) Int. Cl.
*C07D 213/82* (2006.01)
*C07D 213/80* (2006.01)

(52) U.S. Cl.
CPC ......... *C07D 213/82* (2013.01); *C07D 213/80* (2013.01)

(58) Field of Classification Search
CPC .......................... C07D 213/82; C07D 213/80
See application file for complete search history.

(56) References Cited

U.S. PATENT DOCUMENTS

| | | |
|---|---|---|
| 2014/0364604 A1 | 12/2014 | Raillard et al. |
| 2015/0299103 A1 | 10/2015 | Albrecht et al. |
| 2016/0113879 A1 | 4/2016 | Karaborni et al. |
| 2016/0137660 A1 | 5/2016 | Zeidan et al. |
| 2016/0214948 A1 | 7/2016 | Albrecht et al. |
| 2018/0000770 A1 | 1/2018 | Novas et al. |
| 2019/0085008 A1 | 3/2019 | Kluge et al. |

FOREIGN PATENT DOCUMENTS

WO 2017218580 A1 12/2017

OTHER PUBLICATIONS

Pubchem CID 20391231, pp. 1-9, Dec. 5, 2007.
Pubchem CID 10176872, pp. 1-9, Oct. 25, 2006.
Pubchem CID 88804844, pp. 1-10, Feb. 13, 2015.
Pubchem CID 124087394, pp. 1-8, Feb. 18, 2017.
PCT/US2020/028302; Search Report and Written Opinion, dated Aug. 3, 2020, 11 pages.

*Primary Examiner* — Patricia L Morris
(74) *Attorney, Agent, or Firm* — Timothy H. Van Dyke; Wolter, Van Dyke, Davis, PLLC

(57) ABSTRACT

Provided herein are novel monomethyl fumarate prodrugs.

6 Claims, 1 Drawing Sheet

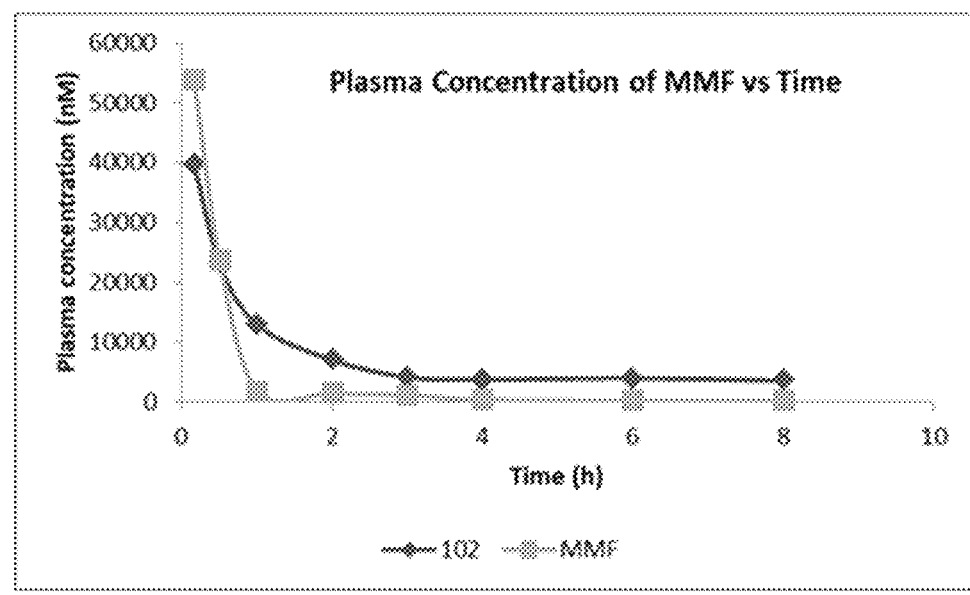

PRODRUGS OF MONOMETHYL FUMARATE

FIELD

The present invention relates to pro-drugs. More particularly, the present invention relates to pro-drugs of monomethyl fumarate, methods for their preparation, pharmaceutical compositions containing these compounds.

BACKGROUND

Dimethyl fumarate (DMF) is known for its anti-inflammatory and cytoprotective properties. It is currently used to treat multiple sclerosis (MS) and psoriasis and is marketed under the name Tecfidera and Fumaderm, respectively. It is well established that on administration, Dimethyl fumarate very quickly converts to monomethyl fumarate (MMF) and that the biological action may be due to MMF.

However, the current treatment involves a very frequent dosing regimen and a very high dosage, which poses problems of patient compliance. Furthermore, it is documented that there is a high degree of interpatient variability with respect to drug absorption and food strongly reduces bioavailability. Absorption is thought to occur in the small intestine with peak levels achieved 5-6 hours after oral administration. Significant side effects occur in 70-90% of patients. In order to improve the pharmacokinetics and inter-patient variability controlled release pharmaceutical compositions comprising fumaric acid esters are known in prior art. Illustrative controlled release formulations may be found in WO 2007/042034, US 2012/0034274 and US 2012/0034303.

Another approach available in the prior art was to obtain different derivatives of fumaric acid, including mono and dialkyl esters (WO 2002/055066 and U.S. Pat. No. 6,355,676). WO 2002/055063, US 2006/0205659 and U.S. Pat. No. 7,157,423 disclose certain amino acid and/or protein-fumarate conjugates. WO 2003/087174 discloses carbocyclic and oxacarbocylic compounds and WO 2006/122652 discloses thiosuccinates. US 20140275048 and US20160228376 also disclose certain derivatives of fumaric acid.

However, the problem of poor pharmacokinetics is yet to be resolved. Hence, there is a need for a new approach so as to decrease the dosing frequency, reduce side-effects and/or improve the physicochemical properties reported in the prior art.

SUMMARY

The present invention provides pro-drugs of monomethyl fumarate formula (I) and its pharmaceutically acceptable salts.

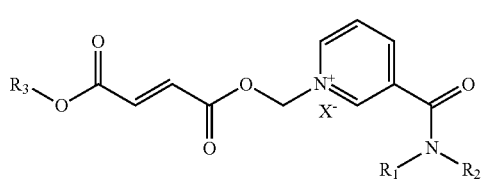

wherein $R_1$ and $R_2$ are independently H, or $C_1$-$C_6$ straight chained alkyl; $R_3$ is a $C_1$-$C_6$ straight chained alkyl; and $X^-$ is the counter ion.

The present invention also discloses a process for synthesis of the compounds of the present invention, pharmaceutical composition comprising the compounds of the present invention and use of the compounds of the present invention. Embodiments of pro-drugs of monomethyl fumarate as described herein have improved pharmacokinetic parameters.

BRIEF DESCRIPTION OF THE FIGURE

FIG. 1 depicts the enhanced pharmacokinetics in delivery of monomethyl fumarate (MMF) by compound 102 of the present invention in comparison with direct administration of MMF.

DETAILED DESCRIPTION

Unless otherwise defined, all technical and/or scientific terms used herein have the same meaning as commonly understood by one of ordinary skill in art. In one embodiment, provided herein are pro-drugs of monomethyl fumarate formula (I) and its pharmaceutically acceptable salts.

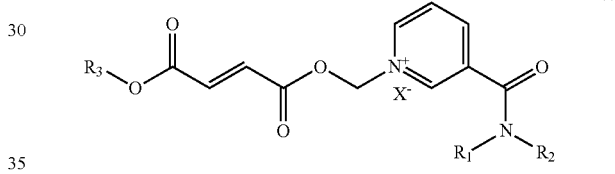

wherein:

$R_1$ and $R_2$ are independently H, or $C_1$-$C_6$ straight chained alkyl; $R_3$ is a $C_1$-$C_6$ straight chained alkyl; and $X^-$ is the counter ion.

The counter ion of the compounds of the present invention may be chosen by selecting the dissociation constant for the drug capable of ionization within the said pH range. By estimating the ionized and un-ionized drug concentration of any compound (using well established equations such a Henderson-Hasselbach equation), the solubility and consequently the absorption of the drug may be modified. Preferably, the counterion is a pharmaceutically acceptable counterion. Suitable counterion include, but not limited to acetate, benzoate, benzylate, bitartrate, bromide, carbonate, chloride, citrate, edetate, edisylate, estolate, fumarate, gluceptate, gluconate, hydrobromide, hydrochloride, iodide, lactate, lactobionate, malate, maleate, mandelate, mesylate, methyl sulfate, mucate, napsylate, nitrate, pamoate (embonate), phosphate and diphosphate, salicylate and disalicylate, stearate, succinate, sulfate, tartrate, tosylate, triethiodide, valerate, and the like.

A few exemplary compounds of the present invention of Formula (I) are provided in Table A:

TABLE A

| Compound No. | Structure | IUPAC Name | SPR NUMBER |
|---|---|---|---|
| 101 | 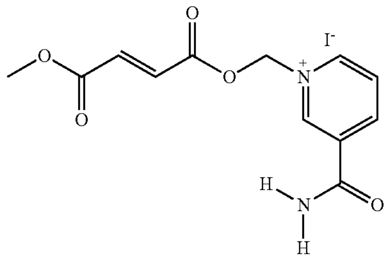 | (E)-3-carbamoyl-1-(((4-methoxy-4-oxobut-2-enoyl)oxy)methyl)pyridin-1-ium iodide | SPR11574 |
| 102 | 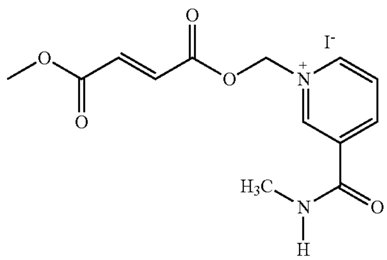 | (E)-1-(((4-methoxy-4-oxobut-2-enoyl)oxy)methyl)-3-(methylcarbamoyl)pyridin-1-ium iodide | SPR11575 |
| 103 | 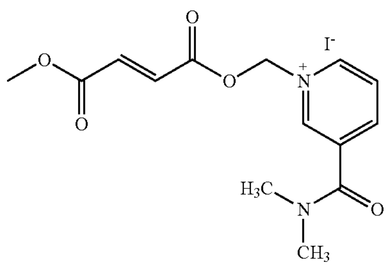 | (E)-3-(dimethylcarbamoyl)-1-(((4-methoxy-4-oxobut-2-enoyl)oxy)methyl)pyridin-1-ium iodide | SPR11576 |
| 104 | 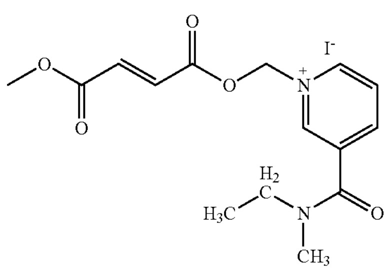 | (E)-3-(ethyl(methyl)carbamoyl)-1-(((4-methoxy-4-oxobut-2-enoyl)oxy)methyl)pyridin-1-ium Iodide | Not Synthesized |
| 105 | 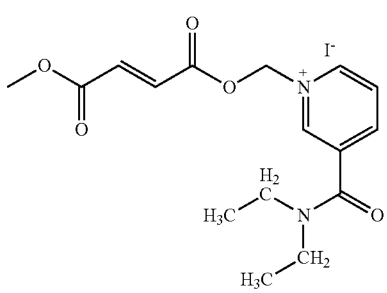 | (E)-3-(ethyl(methyl)carbamoyl)-1-(((4-methoxy-4-oxobut-2-enoyl)oxy)methyl)pyridin-1-ium Iodide | Not Synthesized |
| 106 | 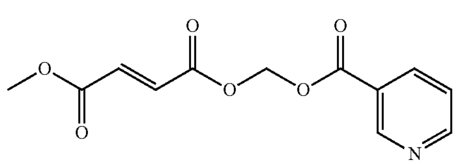 [SMILES: COC(=O)/C=C/C(=O)OCOC(=O)c1cccnc1] | methyl((nicotinoyloxy)methyl)fumarate | SPR11577 |

TABLE A-continued

| Compound No. | Structure | IUPAC Name | SPR NUMBER |
|---|---|---|---|
| 107 | 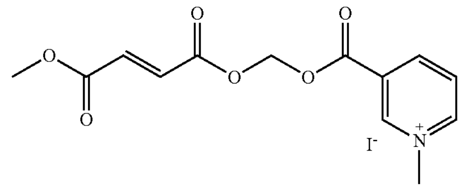 | (E)-3-((((4-methoxy-4-oxobut-2-enoyl)oxy)methoxy)carbonyl)-1-methylpyridin-1-ium iodide | SPR11578 |

The compounds of the present invention are:
(i) (E)-3-carbamoyl-1-(((4-methoxy-4-oxobut-2-enoyl)oxy)methyl)pyridin-1-ium iodide;
(ii) (E)-1-(((4-methoxy-4-oxobut-2-enoyl)oxy)methyl)-3-(methylcarbamoyl)pyridin-1-ium iodide;
(iii) (E)-3-(dimethylcarbamoyl)-1-(((4-methoxy-4-oxobut-2-enoyl)oxy)methyl)pyridin-1-ium iodide;
(iv) (E)-3-(ethyl(methyl)carbamoyl)-1-(((4-methoxy-4-oxobut-2-enoyl)oxy)methyl)pyridin-1-ium iodide;
(v) (E)-3-(diethylcarbamoyl)-1-(((4-methoxy-4-oxobut-2-enoyl)oxy)methyl)pyridin-1-ium iodide
(vi) methyl ((nicotinoyloxy)methyl) fumarate
(vii) (E)-3-((((4-methoxy-4-oxobut-2-enoyl)oxy)methoxy)carbonyl)-1-methylpyridin-1-ium iodide

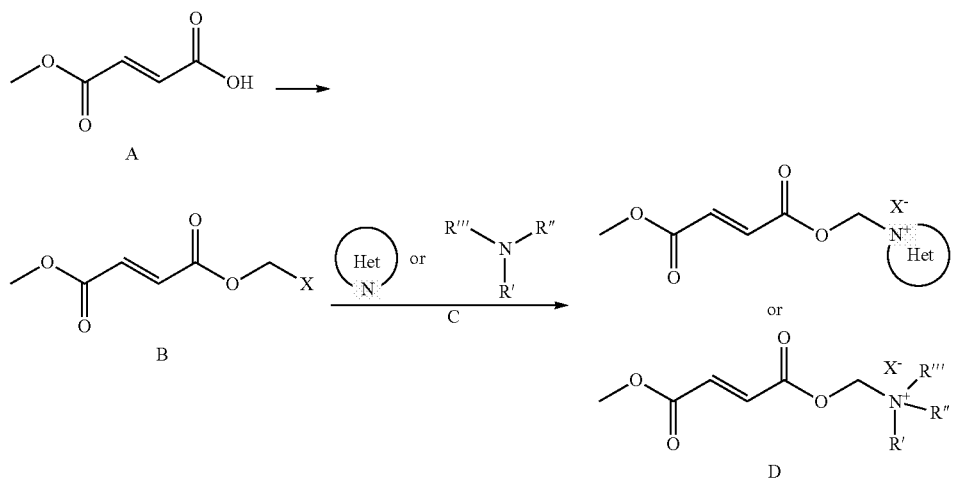

General Schematic Representation of Synthesis of the Compounds of the Present Invention In general compounds of the present invention may be obtained by esterification of the acid A to yield methyl esters, B, that contain a leaving group X, such as chloride or bromide. The conversion of A to B can be done in solvent in the presence of a base such as sodium bicarbonate and an appropriate reagent such as chloromethylchlorosulfate. The reaction may be done at ambient temperature, or under cooling or heating to facilitate the conversion of A to B. The halomethyl esters may be reacted with nitrogen containing heterocycles or appropriate tertiary amines (C) to produce the quarternary salts (D). Example of the nitrogen containing heterocycle can be niacinamide or niacinamide like compounds, substituted niacinamide, nicotinate, or substituted nicotinate to arrive at the compounds of the present invention. The R', R", and R'" of the tertiary amine can be, individually, an alkyl and/or aryl. The esterification process and the quarternisation process may utilize, conditions, reagents, catalysts and solvents as needed for esterification and quarternisation and generally known in the art. X⁻ represents a counterion as described above.

In another embodiment, compositions are provided that contain therapeutically effective amounts of the compound of Formula (I). The compound (e.g., a compound of Formula (I)) and/or an analog thereof can be administered orally, parenterally, (intravenously (IV), intramuscularly (IM), depo-IM, subcutaneously (SC), and depo-SC), sublingually, intranasally (inhalation), intrathecally, transdermally (e.g., via transdermal patch), topically, ionophoretically or rectally. Typically the dosage form is selected to facilitate delivery to the muscle or liver. Dosage forms known to those of skill in the art are suitable for delivery of the compound.

In yet another embodiment, the compounds of the present invention achieves more than simply modifying the pharmacokinetic and physicochemical properties. The advantages of utilizing the compounds of the present invention lies in the ability to use less, overall, of the drug/biologically active compound than would be required of the unmodified drug. This offers several benefits, including potential decrease or even elimination of unwanted side effects and reducing in the dose and the times of administration of the active molecule to the subject in need of the drug.

EXAMPLES

Some embodiments of the invention are herein described, by way of example only, with reference to the accompanying FIGURES. With specific reference now to the FIGURES in detail, it is stressed that the particulars shown are by way of example and for purposes of illustrative discussion of embodiments of the invention. In this regard, the description taken with the FIGURES makes apparent to those skilled in the art how embodiments of the invention may be practiced Example 1: Synthesis of the Compounds of the Present Invention The enumerated compounds of the present invention are synthesized as per scheme 1.
Monomethyl Fumarate (DMT):
Scheme 1:

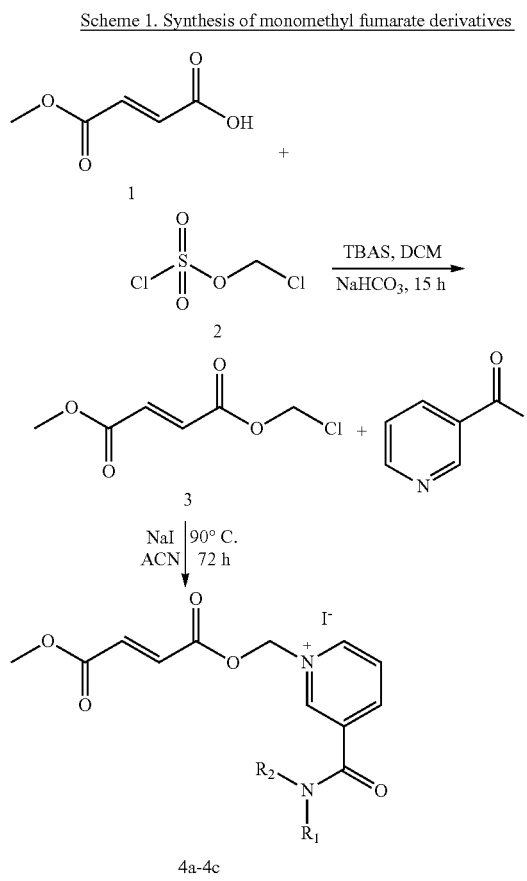

4a-4c
4a) SPR 11574 = $R_1, R_2 = H$
4b) SPR 11575 = $R_1 = H, R_2 = CH_3$
4c) SPR 11576 = $R_1 = CH_3, R_2 = CH_3$

Synthesis of chloromethyl methyl fumarate (3): Monomethyl fumarate (5.0 g, 38.43 mmol) was dissolve in DCM (150 mL). To the solution chloromethyl chlorosulfate (6.34 g, 3.96 mL 38.43 mmol), tetrabutyl ammonium sulfate solution (2.23 g, 2.21 mL, 3.84 mmol) was added and reaction mixture was stirred for 15 min. Sodium bicarbonate (15.21 g, 153.72 mmol) was dissolved in water (150 mL). The aqueous solution of sodium bicarbonate was added drop wise to the reaction mixture and was stirred at room temperature for 15 h.

Work up: After completion of the reaction, reaction mixture was diluted with DCM (100 mL). The organic layer was separated and washed with DM water (150 mL) to remove excess of sodium bicarbonate. Further organic layer was dried over sodium sulfate and concentrated to give crude product Purification: The crude compound was purified by column chromatography over silica gel 100-200 mesh using 8% EtOAc in Hexane as an eluent to give (3.95 g, 58% yield) of compound 3. The liquid compound obtained was solidified as white solid after keeping in refrigerator.

chloromethyl methyl fumarate (Compound-3): White solid, $^1$H NMR (300 MHz, CDCl$_3$); 6.97 (d, J=15.9 Hz, 1H), 6.85 (d, J=15.9 Hz, 1H), 5.81 (s, 2H), 3.83 (s, 3H); $^{13}$C NMR (75 MHz, CDCl$_3$); 164.9, 162.9, 135.4, 131.8, 69.1, 52.5.

Synthesis of (E)-1-(((4-methoxy-4-oxobut-2-enoyl)oxy)methyl)-3-(methylcarbamoyl)pyridin-1-ium iodide derivatives (4b)

Chloromethyl monomethyl fumarate, 3 (2.0 g, 1.12 mmol), sodium iodide (2.52 g, 1.68 mmol) and N-methyl-nicotinamide (0.91 g, 0.674 mmol) were taken in ACN (50 mL) and reaction mixture was stirred at 90° C. for 72 h.

Purification: After completion of the reaction, the reaction mixture was filtered and washed with acetonitrile. The filtrate was concentrated under vacuum to give semisolid crude product. The semisolid crude product was sonicated with solvent (DCM: Ether 9.5:0.5) to break the lump of semisolid. The brown colour solvent was decanted from the mixture to give pale yellow solid product. The process of sonication and decant of brown colour solvents repeated till no colour impurity is present. Further, the yellow solid was washed with ether to give desired product 0.950 g.

(E)-1-(((4-methoxy-4-oxobut-2-enoyl)oxy)methyl)-3-(methylcarbamoyl)pyridin-1-ium iodide (Compound 4b-SPR11575): Yellow solid, 51%; $^1$H NMR (300 MHz, CDCl$_3$); 9.60 (s, 1H), 9.35 (d, J=5.1 Hz, 1H), 9.17 (s, 1H, exchangeable with D$_2$O), 9.04 (d, J=8.10 Hz, 1H), 8.38-8.33 (m, 1H), 6.97-6.91 (m, 1H), 6.84-6.78 (m, 1H), 6.61 (d, J=2.40 Hz, 2H), 3.75 (d, J=2.4 Hz, 3H), 2.88-2.86 (m, 3H), $^{13}$C NMR (75 MHz, CDCl$_3$); 164.5, 163.0, 161.3, 146.8, 145.3, 145.1, 134.9, 133.7, 131.5, 127.8, 79.9, 52.5, 26.4. ESI-MS (C$_{13}$H$_5$N$_2$O$_5^+$.I$^-$), observed (C$_{13}$H$_{15}$N$_2$O$_5$+) 279.00.

HPLC purity: 98.58% By making appropriate change in starting material and using same reaction condition compound 4a and 4c were prepared.

(E)-3-carbamoyl-1-(((4-methoxy-4-oxobut-2-enoyl)oxy)methyl)pyridin-1-ium iodide (Compound 4a-SPR11574): Yellow solid, 76%; $^1$H NMR (300 MHz, CDCl$_3$); 9.62 (s, 1H), 9.36 (d, J=6.30 Hz, 1H), 9.06 (d, J=8.10 Hz, 1H), 8.61 (s, 1H, exchangeable with D$_2$O), 8.38-8.34 (m, 1H), 8.23 (s, 1H, exchangeable with D$_2$O), 6.94 (d, J=15.60 Hz, 1H), 6.81 (d, J=15.90 Hz, 1H), 6.90 (S, 2H), 3.75 (s, 3H); $^{13}$C NMR (75 MHz, CDCl$_3$); 164.5, 162.9, 162.5, 146.9, 145.7, 145.5, 134.8, 133.6, 131.5, 127.8, 79.9, 52.5. ESI-MS (C$_{12}$H$_3$N$_2$O$_5$+.I$^-$), observed (C$_{12}$H$_{13}$N$_2$O+) 265.02.

HPLC purity: 98.00%

(E)-3-(dimethylcarbamoyl)-1-(((4-methoxy-4-oxobut-2-enoyl)oxy)methyl)pyridin-1-ium iodide (Compound 4c-SPR11576): Yellow solid 47%; $^1$H NMR (300 MHz, CDCl$_3$); 9.47 (s, 1H), 9.33 (d, J=4.5 Hz, 1H), 8.83 (d, J=7.20 Hz, 1H), 8.33 (d, J=6.30 Hz, 1H), 6.95 (d, J=15.60 Hz, 1H), 6.81 (d, J=15.90 Hz, 1H), 6.58 (s, 2H), 3.75 (s, 3H), 3.05 (s, 3H), 2.97 (s, 3H); $^{13}$C NMR (75 MHz, CDCl$_3$); 164.5, 163.6, 162.9, 146.0, 145.8, 143.9, 135.8, 134.8, 131.5, 128.1, 79.7, 52.5, 35.1. ESI-MS (C$_{14}$H$_{17}$N$_2$O$_5$+.I$^-$), observed (C$_{14}$H$_{17}$N$_2$O$_5^-$) 293.10.

HPLC purity: 96.71%

Example 2: Compounds SPR11577 and SPR11578 are Synthesized Per Scheme 2

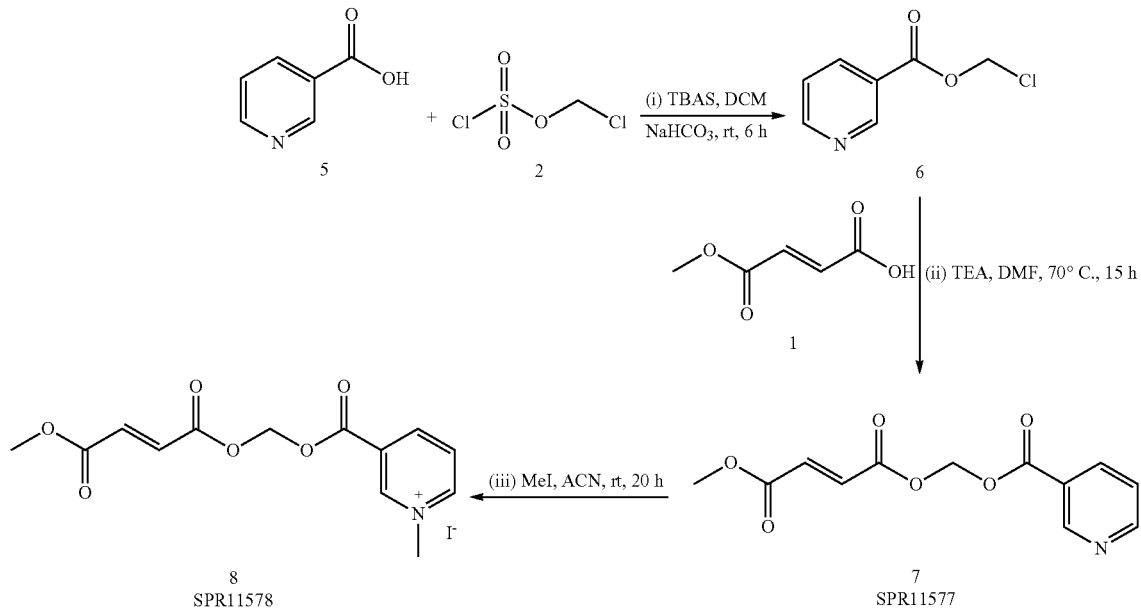

Synthesis of chloromethyl nicotinate (6) Nicotinic acid (1.0 g, 8.13 mmol) was taken in DCM (50 mL). To the solution chloromethyl chlorosulfate (0.789 g, 8.13 mmol), tetrabutyl ammonium sulfate solution (0.472 g, 0.47 mL, 0.813 mmol) was added and biphasic reaction mixture was stirred for 15 min. Sodium bicarbonate (3.21 g, 40.65 mmol) was dissolved in water (70 mL). The aqueous solution of sodium bicarbonate was added drop wise to the reaction mixture and reaction mixture was stirred for 6 h at room temperature.

Work up: After completion of the reaction, the organic layer was extracted in DCM. The extract was washed with DM water to remove extra remains of sodium bicarbonate. Further organic layer was dried over sodium sulfate to give crude product Purification: The crude compound was purified by column chromatography using 10% EtOAc in Hexane as an eluent to give 560 mg, 41%.

Chloromethyl nicotinate (6) $^1$H NMR (300 MHz, CDCl$_3$); 9.06 (s, 1H), 8.66-8.64 (m, 1H), 8.16-8.13 (m, 1H), 7.30-7.25 (m, 1H), 5.83 (s, 2H)

Synthesis of methyl ((nicotinoloxy)methyl) fumarate (Compound 7-SPR11577): Compound 6 (0.657 g, 3.84 mmol), monomethyl fumarate (0.5 g, 3.84 mmol) and triethylamine (0.46 g, 0.65 mL, 4.66 mmol) were taken in DMF (5 mL) and reaction mixture was stirred at 70° C. for 15 h.

Work up: After completion of the reaction, the organic layer was extracted in DMF. The extract was washed with DM water to remove triethylamine. Further organic layer was dried over sodium sulfate to give crude product.

Purification: The crude compound was purified by column chromatography using 25% EtOAc in Hexane as an eluent to give 550 mg; 55%.

methyl ((nicotinoloxy)methyl) fumarate (Compound 7-SPR11577): Yellow solid, $^1$H NMR (300 MHz, CDCl$_3$); 9.26 (d, J=1.2 Hz, 1H), 8.84-8.82 (m, 1H), 8.36-8.32 (m, 1H), 7.46-7.42 (m, 1H), 6.97 (d, J=15.90 Hz, 1H), 6.88 (d, J=15.90 Hz, 1H), 6.13 (s, 2H), 3.82 (s, 3H); $^{13}$C NMR (75 MHz, CDCl$_3$); 164.9, 163.8, 163.4, 151.2, 137.6, 135.3, 132.1, 124.8, 123.5, 80.1, 52.5. ESI-MS ($C_{12}H_{11}NO_6$), observed (M+1) 266.10.

HPLC purity: 99.00%

Synthesis of (E)-3-((((4-methoxy-4-oxobut-2-enoyl)oxy)methoxy)carbonyl)-1-methylpyridin-1-ium iodide (compound 8-SPR11578) Compound 7 (0.55 g, 2.0 mmol) and methyl iodide (0.58 g, 0.25 mL, 4.1 mmol) were taken in acetonitrile (10 ml) and stirred at room temperature for 20 h. The reaction mixture was concentrated under vacuum to give crude compound. The crude compound was washed with Ether and DCM (in the ratio of 9.5:0.5) to give yellow semisolid compound 560 mg, 66%.

(E)-3-((((4-methoxy-4-oxobut-2-enoyl)oxy)methoxy)carbonyl)-1-methylpyridin-1-ium iodide (compound 8-SPR11578): Yellow solid, $^1$H NMR (300 MHz, CDCl$_3$); 9.57-9.43 (m, 2H), 8.96 (d, J=8.10 Hz, 1H), 8.38-8.33 (m, 1H), 6.97-6.78 (m, 2H), 6.16 (m, 2H), 4.71 (s, 3H), 3.81 (s, 3H); $^{13}$C NMR (75 MHz, CDCl$_3$); 164.9, 163.3, 160.2, 149.9, 146.9, 145.3, 135.7, 131.8, 129.1, 128.9, 80.9, 52.6, 50.2. ESI-MS ($C_{13}H_{14}NO_6{}^+I^-$), observed (C13H14NO$_6{}^+$) 280.20.

HPLC purity: 99.14%

Example 3: Evaluation of the Pharmacokinetics of the Compounds of the Present Invention Exemplary compounds of the present invention were subjected to oral (PO) Pharmacokinetics (PK) study in SD rat and data was compared with parent MMF. 6 overnight fasted male SD rats were dosed with MMF dose of 10 mpk and test compounds at the desired dose level of 10 mpk equivalent of MMF by PO route. Dosing vehicle used was MQ water. Blood was collected at different time points by retro orbital route. Plasma samples were stored at −80° C. for LC-MS analysis. Animals were sacrificed post final blood collection. Dosing and collection was done as per the in vivo protocol given below. PK analysis was done using LC-MS (ABI3200). Data analysis was performed using PRISM software to determine PK parameters such Cmax (the maximum (or peak) serum concentration that a drug achieves in a specified compartment or test area of the body after the drug has been administrated and before the administration of a second dose), Tmax (time at which the Cmax is observed) AUC (definite integral in a plot of drug concentration in blood plasma vs. time), MRT (Mean Residence Time) and t1/2 (The time required for one half of the total amount of a particular substance in a biological system to be degraded by biological processes when the rate of removal is nearly exponential)

|  | Protocol |
| --- | --- |
| Test system | SD rat |
| Age | 6-8 weeks |
| Gender | M |
| Body weight range | 200-250 g |
| No. of dose | Once a day (QD), single day |
| Doses | 10 mpk MMF and 10 mpk equivalent of MMF in case of modified drugs |
| No. of animals | 6 overnight fasted animals for each study |
| Route | Oral (PO) |
| Dose formulation | MQ water |
| Route of blood collection | Retro orbital |
| Amount | 40 ul |
| Plasma collection | Centrifugation 1400 rpm, 10 min |
| Plasma storage | −80° C. till processing |

The results are presented at Table 1.

TABLE 1

Pharmacokinetic data of the compounds of the present invention

| Parameters | MMF | SPR11574 | SPR11575 | SPR11576 | SPR11577 | SPR11578 |
| --- | --- | --- | --- | --- | --- | --- |
| Cmax (nM) | 53976.5 | 28802.02 | 43559.5 | 32348.7 | 64775.73 | 20291.3 |
| Tmax (h) | 0.16 | 0.23 | 0.33 | 0.23 | 0.16 | 0.30 |
| AUC (nM · h) | 24435.0 | 16482 | 54522.4 | 17825.8 | 31792.5 | 13482.0 |
| T½ (h) | 1.60 | 1.86 | 5.89 | 4.41 | 1.44 | 0.53 |

The compounds were found to have plasma exposure in rat. Compound 102 (SPR11575) was found to have better enhanced AUC and T1/2 in rat plasma as compared to the parent drug MMF. Animals well tolerated the compounds of the present invention.

The pharmacokinetic parameters, measured as the amount of MMF in blood on direct administration of MMF per se and that on administration of compound 102, is depicted at FIG. 1. From FIGURE it can be clearly seen that the compound 102 releases MMF with an improved MRT in comparison to direct administration of MRT.

Rat Plasma conversion: 11574, 11575, 11576, 11577 convert instantly in rat plasma (ex-vivo). 578 doesn't convert completely ex-vivo and in vivo Solubility: Solubility comparable to monomethyl fumarate, which itself is highly soluble in water Example 4: Stability of Prodrugs

TABLE 2

|  |  | SPR11574 | | SPR11575 | | SPR11576 | | SPR11577 | |
| --- | --- | --- | --- | --- | --- | --- | --- | --- | --- |
|  |  | STORAGE CONDITION | | | | | | | |
| TIME | SOLVENT | RT | RF | RT | RF | RT | RF | RT | RF |
| 0 DAY (14 Nov. 2018) | ACETONITRILE | 97.81 | | 97.7 | | 97.68 | | 99.35 | |
| 7 DAY (21 Nov. 2018) |  | 97.61 | 97.61 | 97.61 | 97.82 | 96.97 | 97.7 | 99.79 | 99.89 |
| 15 DAY (29 Nov. 2018) |  | 97.21 | 97.95 | 97.06 | 97.66 | 96.28 | 97.82 | 100 | 100 |

Compounds dissolved in ACN for analysis
RT: Room temp/25° C.
RF: Refrigeration/4° C.
Table 2 above shows that the molecules have reasonable stability under RT and RF conditions up to 15 days.

What is claimed is:
1. A compound according to the following formula:

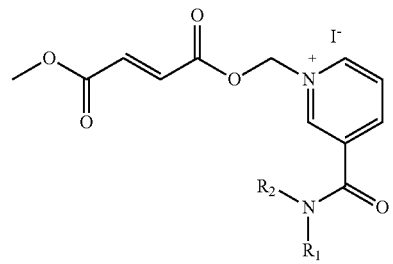

4a-4c
4a) SPR 11574 = $R_1$, $R_2$ = H
4b) SPR 11575 = $R_1$ = H, $R_2$ = $CH_3$
4c) SPR 11576 = $R_1$ = $CH_3$, $R_2$ = $CH_3$ and, optionally, wherein the counterion iodine is substituted with acetate, benzoate, bitartrate, bromide, chloride, citrate, estolate, fumarate, gluceptate, gluconate, lactate, lactobionate, malate, maleate, mandelate, mesylate, methyl sulfate, mucate, nitrate, phosphate, diphosphate, stearate, succinate, sulfate, tartrate, tosylate, or valerate.

2. The compound of claim 1, wherein the compound is

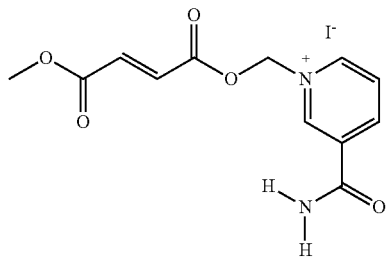

and, optionally, wherein the counterion iodine is substituted with acetate, benzoate, bitartrate, bromide, chloride, citrate, estolate, fumarate, gluceptate, gluconate, lactate, lactobionate, malate, maleate, mandelate, mesylate, methyl sulfate, mucate, nitrate, phosphate, diphosphate, stearate, succinate, sulfate, tartrate, tosylate, or valerate.

3. The compound of claim 1, wherein the compound is

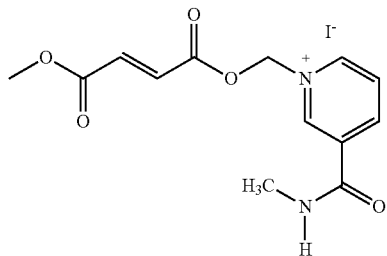

and, optionally, wherein the counterion iodine is substituted with acetate, benzoate, bitartrate, bromide, chloride, citrate, estolate, fumarate, gluceptate, gluconate, lactate, lactobionate, malate, maleate, mandelate, mesylate, methyl sulfate, mucate, nitrate, phosphate, diphosphate, stearate, succinate, sulfate, tartrate, tosylate, or valerate.

4. The compound of claim 1, wherein the compound is

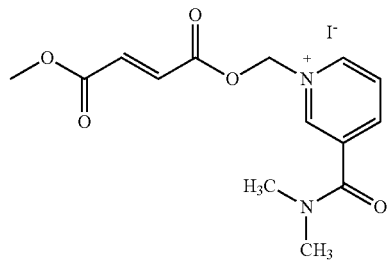

and, optionally, wherein the counterion iodine is substituted with acetate, benzoate, bitartrate, bromide, chloride, citrate, estolate, fumarate, gluceptate, gluconate, lactate, lactobionate, malate, maleate, mandelate, mesylate, methyl sulfate, mucate, nitrate, phosphate, diphosphate, stearate, succinate, sulfate, tartrate, tosylate, or valerate.

5. A compound according to the following formula:

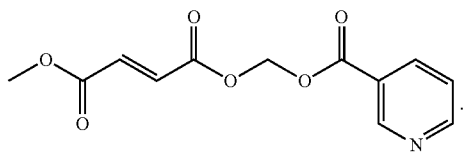

SPR11577

6. A compound according to the following formula:

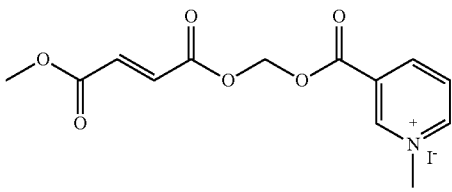

SPR11578 and, optionally, wherein the counterion iodine is substituted with acetate, benzoate, bitartrate, bromide, chloride, citrate, estolate, fumarate, gluceptate, gluconate, lactate, lactobionate, malate, maleate, mandelate, mesylate, methyl sulfate, mucate, nitrate, phosphate, diphosphate, stearate, succinate, sulfate, tartrate, tosylate, or valerate.

* * * * *